United States Patent [19]

Gainutdinova et al.

[11] Patent Number: 4,830,025
[45] Date of Patent: May 16, 1989

[54] INTRAUTERINE CONTRACEPTIVE DEVICE

[75] Inventors: Raisa V. Gainutdinova; Boris A. Jurov; Bentsian M. Mazo; Vera M. Petrova, all of Kazan, U.S.S.R.

[73] Assignee: Nauchno-Proizvodstvennoe Obiedinenie "Medinstrument", Kazan, U.S.S.R.

[21] Appl. No.: 96,485

[22] Filed: Sep. 15, 1987

[51] Int. Cl.4 ................................................ A61F 5/47
[52] U.S. Cl. ....................................... 128/839; 128/830
[58] Field of Search ............... 128/127, 130; 604/265, 604/285

[56] References Cited

U.S. PATENT DOCUMENTS

| | | | |
|---|---|---|---|
| 3,842,826 | 10/1974 | Nolan | 128/130 |
| 3,854,475 | 12/1974 | Bucalo | 128/130 |
| 3,905,360 | 9/1975 | Zaffaroni | 128/130 |
| 3,913,572 | 10/1975 | Wheeler | 128/130 |
| 4,018,220 | 4/1977 | Emmett | 128/130 |
| 4,182,321 | 1/1980 | Csatary | 128/130 |
| 4,198,966 | 4/1980 | Kaivola | 128/130 |
| 4,428,371 | 1/1984 | Krzeminski | 128/127 X |
| 4,562,835 | 1/1986 | Anderson | 128/127 X |
| 4,585,451 | 4/1986 | Millar | 128/127 X |
| 4,628,924 | 12/1986 | Cimber | 128/130 |

OTHER PUBLICATIONS

Lefras, "NOVA-T Cu 200 Ag," 4 pp.

Primary Examiner—Robert A. Hafer
Assistant Examiner—Kevin G. Rooney
Attorney, Agent, or Firm—Fleit, Jacobson, Cohn & Price

[57] ABSTRACT

An intrauterine device includes a transversal member, a rod connected to the transverse member to form a T-shaped element therewith, a coil mounted on the rod, and a thread for dynamic monitoring of the IUD in the uterine cavity, the thread being passed over the transversal member at the place where the transversal member is connected to the rod and being interposed between the rod and the coil lengthwise the former.

2 Claims, 1 Drawing Sheet

4,830,025

INTRAUTERINE CONTRACEPTIVE DEVICE

TECHNICAL FIELD

The present invention relates generally to contraceptives and more specifically to intrauterine devices (IUD).

BACKGROUND OF THE INVENTION

Known in the art is an intrauterine device (U.S. Pat. No. 4,198,966), comprising a strip, a rod connected to the strip to form a T-shaped element, a copper coil mounted onto the rod, and a thread fixed at the rod end and adapted for dynamic monitoring.

Another prior-art intrauterine device Nova T Cu 200 Ag (Huhtamäki Co., Leiras, Finland) is known comprising a strip, a rod connected to the strip to form a T-shaped element, a copper-wire coil with a silver base, mounted onto the rod, and a thread for dynamic monitoring of the IUD in the uterine cavity, fixed at the rod end.

The aforementioned known devices are characterized by the fact that the dynamic monitoring thread fixed at the rod end through a double knot and hanging over the cervical canal, causes irritation of the uterine portion located above the cervix and, hence, contraction of the uterine muscles and expulsion of the device from the uterus.

SUMMARY OF THE INVENTION

It is therefore an object of the invention to reduce expulsion of the device.

It is another object of the invention to reduce the degree of trauma inflicted.

The object mentioned above may be accomplished in an intrauterine device comprising a transversal member, a rod interconnected to the transversal member to form a T-shaped element, a coil mounted on the rod, and a thread for dynamic monitoring of the IUD in the uterine cavity, wherein according to the invention, the thread is passed over the transversal member at the place where the transversal member is joined with the rod, and is interposed between the rod and the coil lengthwise the former.

It is also expedient that the transversal member of the intrauterine device be provided with a groove located on its portion adjoining the rod, said groove being adapted for the thread to accommodated.

The aforesaid construction arrangement of the intrauterine device makes it possible to dispense with a knot formed when holding the dynamic monitoring thread to the rod, said thread being as a rule made from polyamide or polypropylene filaments. This reduces traumatization of the internal uterine orifice and renders the expulsion of IUD less liable to occur.

BRIEF DESCRIPTION OF DRAWINGS

In what follows the invention is illustrated in some specific embodiments thereof to be read with reference to the accompanying drawings, wherein.

BEST MODE FOR CARRYING OUT THE INVENTION

Figure 1:
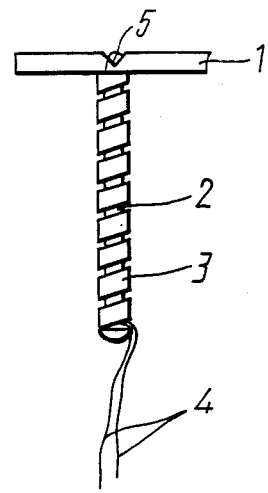
FIG. 1 is a general schematic view of an intrauterine device, according to the invention.
Figure 2:
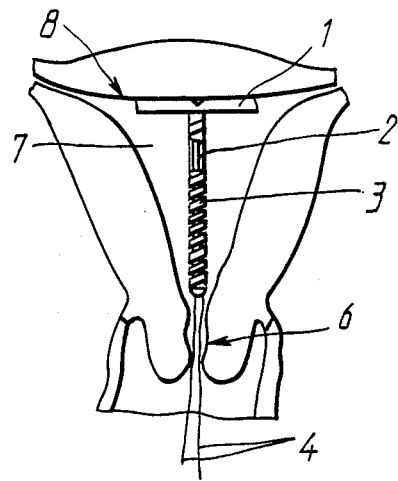
FIG. 2 illustrates the IUD as inserted in the uterine cavity, according to the invention.

The intrauterine device (FIGS. 1, 2) comprises a transversal member 1, a rod 2, which is interconnected with the transversal member 1 to form a T-shaped element therewith, and a coil mounted on the rod 2. A single dynamic monitoring thread 4 is passed over the transversal member 1 at the place where the transversal member 1 is connected to the rod 2 to form a connection between the transversal member and the rod and is accommodated in a groove 5 between the rod 2 and the coil 3 lengthwise the rod 2 and frictionally engaged by the rod and the coil, while the thread free ends hang from a cervical canal 6.

The intrauterine device of the invention operates as follows.

The IUD preliminarily arranged in a straight line by putting the transversal member 1 in alignment with the rod 2, together with the coil 3 and the dynamic monitoring thread 4, is fitted into a special syringe (not shown in the Drawing.) Then the IUD is inserted directly into a uterine cavity 7 (FIG. 2), wherein the device assumes the position that suits the shape of the uterine body. When in the uterine cavity 7 the device is pressed by the transversal member 1 against an uterine fundus 8, while the free ends of the dynamic monitoring thread 4 emerge from the cervical canal 6.

Provision of a novel mutual arrangement of the dynamic monitoring thread 4 and the rod as described above renders the device atraumatic and the expulsion of the device less possible.

Industrial Applicability

The invention can be applied in gynecology for prevention of an undesirable pregnancy, as well as a prevention measure aimed at birth control and family planning.

What is claimed is:

1. An intrauterine device, comprising:
   a transversal member;
   a rod connected to said transversal member to form a T-shaped element therewith;
   a coil mounted on said rod to surround said rod;
   a single dynamic monitoring thread passed over said transversal member at the place where said transversal member is connected to said rod to form a connection between said transversal member and said rod, and said thread being interposed between and frictionally engaged by said rod and said coil along the length of said rod to allow the intrauterine device to lie in a straight line with said transversal member extending in alignment with said rod prior to insertion of the intrauterine device into the uterine cavity and so that the intrauterine device can assume the shape of the uterine cavity when in the uterine cavity and remain atraumatic even when said transversal member is connected to said rod in the uterine cavity.

2. An intrauterine device as defined in claim 1, wherein:
   a groove in said transversal member on a portion of said transversal member adjoining said rod is adapted to accommodate said thread passed over said transversal member.

* * * * *